(12) United States Patent
McLaughlin et al.

(10) Patent No.: US 7,374,677 B2
(45) Date of Patent: May 20, 2008

(54) TWO STAGE HEMOFILTRATION THAT GENERATES REPLACEMENT FLUID

(75) Inventors: Jennifer K. McLaughlin, Valley Center, CA (US); Don Schoendorfer, Santa Ana, CA (US)

(73) Assignee: KKJ, Inc., Valley Center, CA (US)

( * ) Notice: Subject to any disclaimer, the term of this patent is extended or adjusted under 35 U.S.C. 154(b) by 430 days.

(21) Appl. No.: 10/922,763

(22) Filed: Aug. 20, 2004

(65) Prior Publication Data

US 2006/0041216 A1 Feb. 23, 2006

(51) Int. Cl.
  *B01D 61/18* (2006.01)
  *B01D 61/14* (2006.01)
  *B01D 63/06* (2006.01)
  *B01D 63/16* (2006.01)

(52) U.S. Cl. ............ 210/321.67; 210/194; 210/195.1; 210/195.2; 210/252; 210/257.1; 210/257.2; 210/295; 210/321.6; 210/321.63; 210/321.68; 210/321.71; 604/4.01; 604/5.02; 604/5.04; 604/6.07; 604/6.09

(58) Field of Classification Search .............. 210/194, 210/195.1, 195.2, 252, 256, 257.1, 257.2, 210/295, 321.6, 321.63, 321.67, 321.68, 210/321.71; 604/4.01, 5.01, 5.04, 6.01, 6.07, 604/6.09
See application file for complete search history.

(56) References Cited

U.S. PATENT DOCUMENTS

| | | |
|---|---|---|
| 3,619,423 A | 11/1971 | Galletti et al. |
| 4,230,564 A | 10/1980 | Keefer et al. |
| 4,670,176 A | 6/1987 | Morioka et al. |
| 4,675,106 A | 6/1987 | Schoendorfer et al. |
| 4,729,837 A | 3/1988 | Henricson |
| 4,740,331 A | 4/1988 | Phillips et al. |
| 4,753,729 A | 6/1988 | Schoendorfer et al. |
| 4,790,942 A * | 12/1988 | Shmidt et al. .............. 210/650 |
| 4,816,151 A | 3/1989 | Schoendorfer et al. |
| 4,871,462 A | 10/1989 | Fischel et al. |
| 4,876,013 A | 10/1989 | Shmidt et al. |
| 5,000,848 A | 3/1991 | Hodgins et al. |
| 5,034,135 A | 7/1991 | Fischel |

(Continued)

FOREIGN PATENT DOCUMENTS

DE 4015187 11/1990

(Continued)

OTHER PUBLICATIONS

Sangho Lee and Richard M. Lueptow, *Mass Transfer and Concentration Polarization in Rotating Reverse Osmosis* (2001).

*Primary Examiner*—John Kim
(74) *Attorney, Agent, or Firm*—Knobbe Martens Olson & Bear LLP (57) ABSTRACT

The present invention relates to a system for two-stage blood dialysis of a patient. In one embodiment, the system comprises a first filtration device for receiving the blood from the patient and for producing a first filtrate and processed blood. The system further comprises a second filtration device for receiving the first filtrate and producing replacement fluid and waste product. At least one of the first and second filtration devices preferably comprises a Taylor vortex-enhanced blood filtration device.

11 Claims, 6 Drawing Sheets

U.S. PATENT DOCUMENTS

| | | | |
|---|---|---|---|
| 5,053,121 A * | 10/1991 | Schoendorfer et al. | 210/90 |
| 5,194,145 A | 3/1993 | Schoendorfer | |
| 5,738,792 A | 4/1998 | Schoendorfer | |
| 5,900,142 A | 5/1999 | Maloney et al. | |
| 6,033,561 A * | 3/2000 | Schoendorfer | 210/195.1 |
| 6,099,730 A | 8/2000 | Ameer et al. | |
| 6,475,071 B1 | 11/2002 | Joslyn | |
| 2003/0146154 A1 | 8/2003 | Moriarty et al. | |
| 2003/0146157 A1 * | 8/2003 | Lueptow | 210/652 |
| 2004/0238445 A1 | 12/2004 | McLaughlin et al. | |

FOREIGN PATENT DOCUMENTS

| | | |
|---|---|---|
| DE | 41 02 693 A1 | 8/1992 |
| DE | 42 24 963 A1 | 2/1994 |
| GB | 1480406 | 7/1977 |
| WO | WO 9925463 | 5/1999 |
| WO | WO 03066200 | 8/2003 |
| WO | WO 2004007048 | 1/2004 |

* cited by examiner

TWO STAGE HEMOFILTRATION THAT GENERATES REPLACEMENT FLUID

BACKGROUND OF THE INVENTION

1. Field of the Invention

Preferred aspects of the present invention relate to multistep filtrations wherein successive filtrations remove filtrates of various specifications. Preferred embodiments of the present invention are particularly useful to regenerate fluid lost during blood dialysis.

2. Description of the Related Art

Traditionally, dialysis is the maintenance therapy used to treat kidney disease. There are two common approaches. One is peritoneal dialysis, wherein the process is done internally to the patient, in the patient's pericardium. Peritoneal dialysis uses the patient's abdominal lining as a blood filter. The abdominal cavity is filled with dialysate, thereby creating a concentration gradient between the bloodstream and the dialysate. Toxins diffuse from the patient's blood stream into the dialysate, which must be exchanged periodically with fresh dialysate.

The second approach is by filtration dialysis. Filtration dialysis encompasses two main filtration techniques: hemodialysis and hemofiltration. Both operate extracorporeally by removing the patient's blood, treating the blood to remove toxins, and returning the processed blood to the patient. Yet, each process functions by a different physical separation technique.

Hemodialysis effects removal of toxins from blood by diffusion. The patient's blood flows past one side of a membrane while dialysate flows past the other side. The membrane selectively allows for the flux of small molecules. Due to the concentration gradient between the blood and the dialysate, small molecule toxins diffuse into the dialysate. At the same time, nutrients, such as electrolytes and other chemicals, present in the dialysate diffuse into the blood. The processed blood is then returned to the patient.

Hemofiltration effects removal of toxins from blood by convection. The patient's blood is passed through a filter that is permeable to plasma water and, generally, molecules smaller than 20,000 Daltons. The resulting plasma water filtrate, called "blood-waste," contains water, the toxic blood components, and "small desirable molecules," including small molecule nutrients and electrolytes. Since the processed blood lacks vital components lost through filtration, and since its volume is substantially reduced, a replacement fluid must be added to the processed blood before its reintroduction to the patient. Depending on the hemofiltration needs, the replacement fluid can be added pre- or post-hemofiltration.

In addition to these two blood purification techniques, methods combining hemodialysis and hemofiltration, known as hemodiafiltration, have been used. Hemodiafiltration effects removal of toxins from blood by both diffusion and convection. As in hemofiltration, blood volume and nutrients/electrolytes must be replaced with replacement fluid in hemodiafiltration procedures.

Generally, replacement fluid is engineered to mimic healthy plasma water with respect to pH, electrolyte and nutrient concentration. However, the replacement fluid may also be adjusted to correct for abnormalities in the individual patient. Biologically compatible buffers, such as citrate, lactate, acetate and bicarbonate, often serve as the base for replacement fluids. The buffers may then be supplemented with electrolytes, such as chloride, sodium, calcium, magnesium, potassium, and phosphate, and nutrients, such as glucose and dextrose, as required by the patient.

Disadvantages of these blood processing methods include the difficulties and costs associated with the production of a large amount of replacement fluid that is free of contaminants harmful to the patient. In addition, hemodialysis, hemofiltration and hemodiafiltration create a substantial amount of medical waste that is costly to dispose of. Consequently, there exists a need to recycle the waste from these systems to generate bio-compatible, low cost replacement fluid or dialysate. Thereby, the need for the production of large volumes of foreign dialysate or replacement fluid may be eliminated. Filtration of the patient's blood-waste generated during blood dialysis meets these needs.

Another problem faced by those using well-known methods of blood dialysis is filter clogging, described as "concentration polarization." As a result of the selective permeability properties of a filter, filtered material that cannot pass through the filter often becomes concentrated on the surface of the filter. This phenomenon is clearly illustrated by the case of a "dead-end" filter, such as a coffee filter. During the course of the filtration process, the filtered material (coffee grounds) building up on the filter creates flow resistance to the filtrate, the fluid (coffee), which can pass through the filter. Consequently, filtrate flux is reduced, and filtration performance diminishes.

Various solutions to the problem of concentration polarization have been suggested. These include: increasing the fluid velocity and/or pressure (see e.g., Merin et al., (1980) *J. Food Proc. Pres.* 4(3):183-198); creating turbulence in the feed channels (Blatt et al., *Membrane Science and Technology*, Plenum Press, New York, 1970, pp. 47-97); pulsing the feed flow over the filter (Kennedy et al., (1974) *Chem. Eng. Sci.* 29:1927-1931); designing flow paths to create tangential flow and/or Dean vortices (Chung et al., (1993) *J. Memb. Sci.* 81:151-162); and using rotating filtration to create Taylor vortices (see e.g., Lee and Lueptow (2001) *J. Memb. Sci.* 192:129-143 and U.S. Pat. Nos. 5,194,145, 4,675,106, 4,753,729, 4,816,151, 5,034,135, 4,740,331, 4,670,176, and 5,738,792, all of which are incorporated herein in their entirety by reference thereto). In U.S. Pat. No. 5,034,135, Fischel discloses creating Taylor vorticity to facilitate blood fractionation. Fischel also describes variations in the width of the gap between a rotary spinner and a cylindrical housing, but does not teach variation in this width about a circumferential cross-section.

Taylor vortices are induced in the gap between coaxially arranged cylindrical members when the inner member is rotated relative to the outer member. Taylor-Couette filtration devices generate strong vorticity as a result of centrifugal flow instability ("Taylor instability"), which serves to mix the filtered material concentrated along the filter back into the fluid to be processed. Typically, a cylindrical filter is rotated within a stationary outer housing. It has been observed that membrane fouling due to concentration polarization is very slow compared to dead-end or tangential filtration. Indeed, filtration performance may be improved by approximately one hundred fold.

The use of Taylor vortices in rotating filtration devices has been applied to the separation of plasma from whole blood (See, e.g., U.S. Pat. No. 5,034,135). For this application, the separator had to be inexpensive and disposable for one-time patient use. Further, these separators only had to operate for relatively short periods of time (about 45 minutes). Moreover, the separator was sized to accept the flow rate of blood that could reliably be collected from a donor (about 200 ml/minute). This technology provided a significant improvement to the blood processing industry. The advantages and improved filtration performance seen with rotating filtration systems (Taylor vortices) have not been explored in other areas of commercial fluid separation—including kidney dialysis Consequently, an improved blood dialysis system may be configured to significantly reduce the artificial replacement fluids necessary. In addition, this improved blood dialysis system may produce Taylor vortices to alleviate the problem of concentration polarization so prevalent with known methods of filtration.

SUMMARY OF THE INVENTION

In one embodiment, the present invention relates to a system for two-stage blood dialysis of a patient. The system comprises a first filtration device for receiving the blood from the patient and producing a first filtrate and processed blood. The system further comprises a second filtration device for receiving the first filtrate and producing replacement fluid and waste product. At least one of the first and second filtration devices preferably comprises a Taylor vortex-enhanced blood filtration device.

In another embodiment, the present invention relates to another system for two-stage blood dialysis of a patient. The system comprises a dialysis device for receiving the blood from the patient and dialysate and producing waste dialysate and processed blood. The system further comprises a filtration device for receiving the waste dialysate and producing recycled dialysate and waste product.

In another embodiment, a method for performing hemodialysis on a patient may be implemented in accordance with the present invention. A first filtration device configured to create Taylor vorticity is provided, and a second filtration device is also provided. Blood is introduced from the patient into the first filtration device, and a first filtrate from the first filtration device is introduced into the second filtration device. A replacement fluid may then be obtained from the second filtration device.

In another embodiment, a second method for performing hemodialysis on a patient may be implemented in accordance with the present invention. A first filtration device is provided, and a second filtration device configured to create Taylor vorticity is also provided. Blood is introduced from the patient into the first filtration device, and a first filtrate from the first filtration device is introduced into the second filtration device. A replacement fluid may then be obtained from the second filtration device.

In another embodiment, another method for performing hemodialysis on a patient may be implemented in accordance with the present invention. A dialysis device and a filtration device are provided. Blood is introduced from the patient into the dialysis device, and waste dialysate from the dialysis device is introduced into the filtration device. A recycled dialysate may then be obtained from the filtration device.

DETAILED DESCRIPTION OF THE PREFERRED EMBODIMENT

Traditionally, blood dialysis procedures are single stage. In other words, the blood is removed from the patient, processed through a single filtration device to remove waste products, and returned to the patient. Unfortunately, blood is a heterogeneous fluid with molecules that are both smaller and larger than these waste products, which are generally in the range of 300-6,000 Daltons. As a result, filtration devices that remove the waste products from blood often inadvertently remove many of those smaller molecules, e.g. water and electrolytes, in the process. These smaller molecules must then be replaced prior to reintroduction of the blood to the patient.

In typical machines, blood is pumped from the patient at 300-450 mL/min. Approximately half of this flow is filtered from the blood and disposed of as blood-waste. In a 3 hour procedure, between 20 and 30 liters of replacement fluid must therefore be added to the blood flow in order to keep the patient's blood volume constant. Of course, the majority of the filtrate in such a procedure comprises water and other small, desirable molecules.

One embodiment of the present invention contemplates using a multi-stage filtration process to recapture much of this desirable filtrate and combine it with the processed blood in order to improve the blood volume returning to the patient without using excessive volumes of artificial replacement fluid. In one embodiment, a two-stage filtration process is employed. In the first stage, a filtration device, like that in the prior art, is used that is permeable to water, small nutrient molecules and waste products. In the second stage, blood-waste emerging from this first stage filtration device is sent through a second filtration device that filters the larger waste product molecules. The plasma water filtrate emerging from the second filtration device can then be used as clean, bio-compatible replacement fluid to increase the blood volume returning to the patient. Of course, in other embodiments, more stages may be necessary to filter out particular waste products from other, similarly sized molecules.

Figure 1:
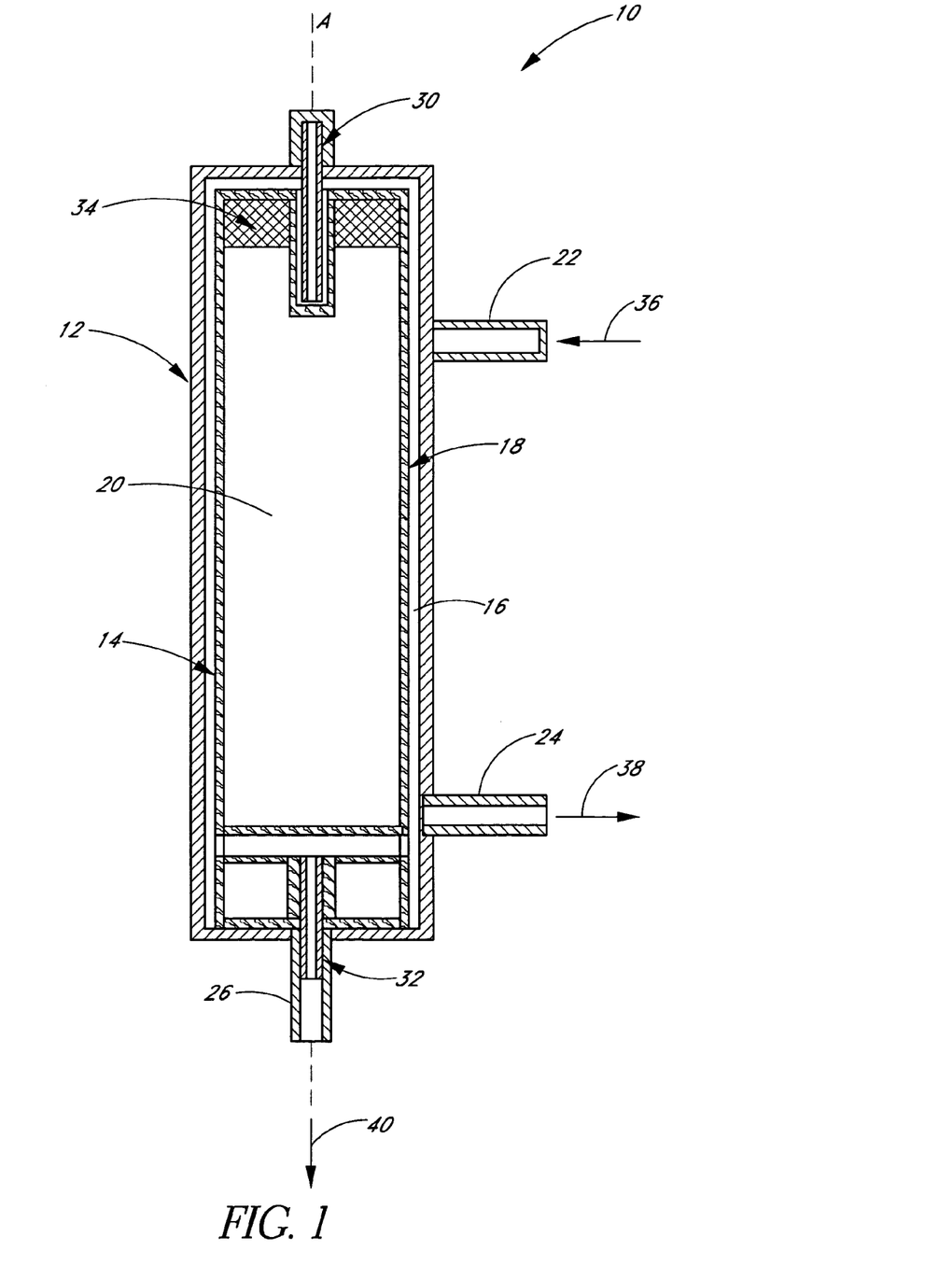
FIG. 1 shows a cross sectional view of one embodiment of a vortex-enhanced blood dialysis device for use with the present invention.

A variety of filtration devices may be used to perform either the first or second stages of one embodiment of the present invention. FIG. 1 shows a cross section of one possible filtration device 10 to be used in the present invention. In this filtration device, a single rotor creates Taylor vorticity. In the illustrated embodiment, the filtration device 10 is used to perform hemodialysis, filtering molecules of a certain size (including waste products) from blood. In other embodiments, the device 10 may be used, more generally, to transfer mass from one fluid. In still other embodiments, the device 10 may be used to transfer heat from one fluid. As would be well known to those of skill in the art, the invention should not be limited to medical applications.

In one embodiment, the filtration device 10 comprises a cylindrical case 12 housing a cylindrical rotor 14. A gap 16 exists between the case 12 and the rotor 14, and, in a preferred embodiment, the rotor 14 is disposed coaxially within the cylindrical case 12. In other embodiments, different geometries and configurations may be chosen for the case and rotor, to accommodate other fluids and other means of generating Taylor vorticity.

In the illustrated embodiment, the cylindrical, circumferential walls of the rotor 14 are at least partially composed of a filtration membrane 18, and partially define a rotor interior 20. The rotor interior 20 is further defined by the top and bottom walls of the rotor 14, which may or may not comprise filtration membrane. As illustrated in FIG. 1, the filtration membrane 18 may be used for the first stage of a two-stage dialysis method. The filtration membrane acts as a dialysis membrane, porous to water, electrolytes, small nutrient molecules and the small to medium-sized molecules that make up waste products present in blood. In a typical application, the dialysis membrane 18 is porous up to a mass of approximately 10,000 Daltons. In another application, the dialysis membrane 18 may be more or less porous, in the range of 6,000 to 20,000 Daltons. In another embodiment, the filtration membrane may be used for the second stage of the two-stage dialysis method. The filtration membrane might then be permeable for molecules up to a mass of approximately 300 Daltons. Thus, plasma water, electrolytes and small nutrient molecules would flow through as filtrate into the rotor interior 20, and the heavier waste products would be filtered out. In other embodiments, varying degrees of filtration and/or heat transfer may be facilitated by the use of different filtration membranes. For example, in a heat transfer application, the filtration membrane may comprise an impermeable structure, which nevertheless is an effective transferor of heat.

In the illustrated embodiment, the cylindrical case 12 has three fluid access ports 22, 24, 26; two 22, 24 leading to and from the gap 16 between the case 12 and rotor 14, and one 26 leading from the rotor interior 20. In other embodiments, different fluid access configurations may be provided. For example, in one embodiment, only one fluid access port leads to the gap between the case and rotor, and two ports may lead to the rotor interior.

In one embodiment, mounted in the axis A of the cylindrical case 12 are two pivot pins 30, 32, one on either end. These pivot pins 30, 32 define the axis of rotation A for the rotor 14 and facilitate the free rotation of this rotor 14. As illustrated, the bottom pivot pin 32 may be hollow, allowing fluid transport passage through the case 12 and rotor 14. Of course, in other embodiments, the top pivot pin 30 may also be hollow to accommodate another fluid access port. Other means of facilitating rotation may be provided, including, e.g., ball-bearing assemblies and other means well known to those of skill in the art.

In one embodiment of the invention, the rotor 14 can rotate freely within the cylindrical case 12. In order to control this rotation, a spinner magnet 34 may be mounted internally to the rotor 14, and an external rotating magnetic field (not shown) may be configured to interact with this spinner magnet 34. By modulating the external magnetic field, the magnet 34 and, in turn, the rotor 14 can be made to spin in different directions and at varying speeds. In a preferred embodiment of the invention, the rotor 14 can be spun at a speed sufficient to create Taylor vorticity within a fluid in the gap 16 between the rotor 14 and case 12. By creating Taylor vorticity in this gap 16, filtration performance can be dramatically improved. Other means of spinning the rotor 14 in order to create Taylor vorticity may be used in keeping with this invention, as is known to those of skill in the art. For example, in one embodiment, a motor may be attached to at least one of the pivot pins, e.g. the top pivot pin 30, attached to the rotor 14.

In one embodiment, the rotating magnetic fields that control the rotor 14 can be produced by a series of magnetic coils that surround the filtration device 10 at its top. These electrical coil assemblies can be formed in half arch ("C" sections) that can be closed around the device 10, although other configurations are possible.

The illustrated size of the device 10 is considered adequate for hemodialysis, although in other applications, larger or smaller filtration devices may be utilized to suit the particular fluids being processed.

In a hemodialysis application, the gap 16 between the rotor 14 and inside wall of the case 12 is selected to provide adequate Taylor vorticity in the blood. This gap 16 depends on the diameter and the RPM of the rotor 14, which parameters can be modified by one of skill in the art. With a centrifugal speed in the range of about 2000-5000 RPM and a rotor diameter of about 0.1 to 10 inches, the width adequate to generate Taylor vortices may be in the range of about 0.003 to about 0.3 inches. More preferably, a gap 16 having a width of about 0.03 inches should provide adequate vorticity for a rotor 14 of about 1 inch in diameter spun at about 2,400 RPM. In a preferred embodiment of the filtration device 10, the rotor has a diameter of approximately 2 inches and is slightly longer than 6 inches.

Figure 2:
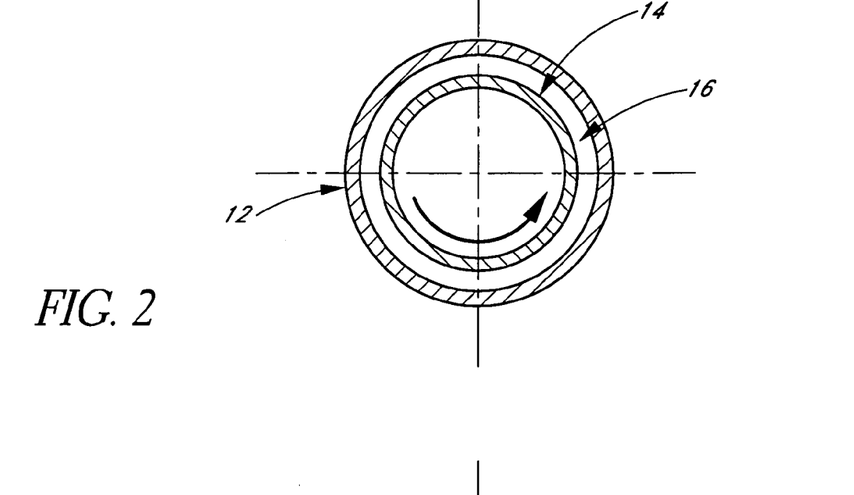
FIG. 2 shows an overhead cross sectional view of one embodiment of the device of FIG. 1.
Figure 3:
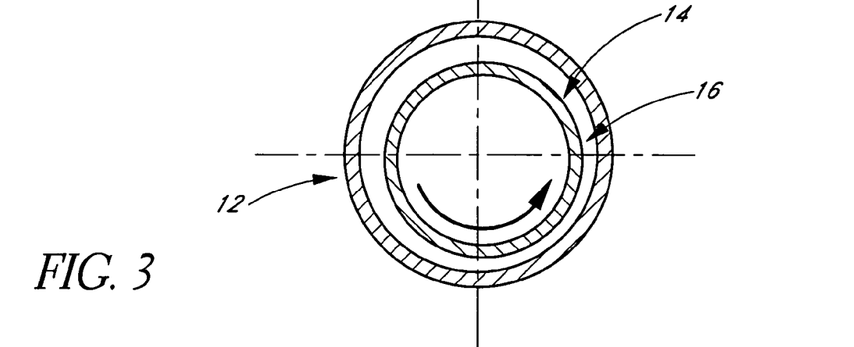
FIG. 3 shows an overhead cross sectional view of a second embodiment of a vortex-enhanced dialysis device.
Figure 4:
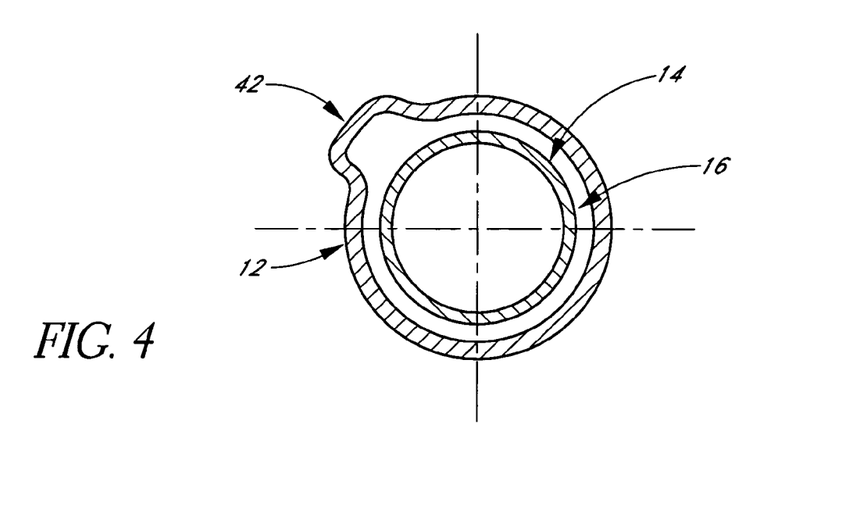
FIG. 4 shows an overhead cross sectional view of a third embodiment of a vortex-enhanced dialysis device.

FIGS. 2-4 illustrate some further structural features of different embodiments of the hemodialysis device described above for use in the two-stage filtration process. In particular, different geometries and configurations of the housing and rotor are shown, which may be implemented to attain various advantages. In FIG. 2, the embodiment described above is shown. As can be more clearly seen in this Figure, the rotor 14 is cylindrical and disposed coaxially within the cylindrical case 12. Thus, the gap 16 is of constant width about the circumference of the device 10. In this relatively simple embodiment, calibrating the appropriate speed of the rotor 14 is more easily accomplished, and the Taylor vortices are fairly constant in strength about the entire filtration membrane 18.

In FIG. 3, another configuration of the case 12 and rotor 14 is shown. In this embodiment, the case 12 and rotor 14 have individual cross-sections similar to those in FIG. 2, but are no longer aligned coaxially. As shown in FIG. 3, the gap 16 therefore varies in width about the circumference of the case 12. Since the Taylor number, reflecting the strength of resulting vortices, is directly proportional to the width of the gap, the sections of rotor 14 farther from the wall of the case 12 experience greater Taylor vorticity than those sections nearer to the wall. As the rotor 14 passes these wider gap locations, residual concentration polarization and any clogging of the filter membrane 18 will be "blown" off by the stronger vortices, opening up blinded zones in the membrane 18. As a result, once per revolution, the longitudinally extending sections of the membrane 18 will be "cleaned" by passing the widened portions of the gap 16, and the efficiency of the device 10 may be improved. In addition, where the width of the gap 16 decreases, the shear forces in the gap increase, and this varying shear force may also tend to increase mass transport across the membrane 18. Thus, once per revolution, we can increase shear and decrease vorticity at any point on the membrane 18 on rotor 14.

In FIG. 4, another configuration of the case 12 and rotor 14 is shown that will similarly create a non-constant width gap. In this configuration, the case 12 and rotor 14 are configured similarly to those in FIG. 2, but the case 12 further has a bulge 42 incorporated into its wall. The gap 16 therefore varies in width about the circumference of the case 12, widening at the site of the bulge 42, producing the advantages discussed above with reference to FIG. 3. The abrupt shift between wide and narrow widths in this embodiment may introduce further vortex characteristics that may facilitate dialysis. In other embodiments, the case 12 and rotor 14 may have other cross-sectional geometries, resulting in a variable width gap 16.

Returning to FIG. 1, one method of implementing the hemodialysis device 10 may be discussed with reference to the Figure. Arrows 36, 38 and 40 show the input and output of the flows into and out of the device 10. In the illustrated embodiment, blood from a patient flows through the gap 16 between the rotor 14 and the case 12, while water, small nutrient molecules, electrolytes and waste products are filtered into the rotor interior 20. Due to the concentration gradient between the blood and the plasma water that initially crosses the membrane 18, certain waste products will preferentially flow through the dialysis membrane 18 into the plasma water, thereby dialyzing the blood. The rotor 14 spins at a speed sufficient to create Taylor vortices in the blood and prevents concentration polarization in the blood near the dialysis membrane 18. In this way, one embodiment of the present invention enables use of a smaller, more biocompatible hemodialysis device 10.

In further detail, a blood inlet port 22 is located at the top of the cylindrical case 12 and a blood outlet port 24 is located at the bottom. This allows blood to flow from top to bottom simply using gravitational energy, and pressure from the blood influx. The device 10 is preferably designed such that in the time it takes a certain quantity of blood to travel from the top of the hemodialysis device 10 to the bottom, the desired amount of waste by-product has been extracted. A water and waste by-product outlet port 26 is located at the bottom of the rotor 14. In a preferred embodiment, this solution flows out of the device 10 for further filtering as described in further detail below.

In another embodiment, a dialysis fluid may be used to facilitate hemodialysis. Another fluid access port may be added to the top of the device 10 to allow dialysis fluid to enter the device. As is described in detail with reference to FIG. 6, waste products diffuse into the dialysis fluid and are carried away from the device by the dialysate flow. Other modifications may also be made in keeping with the present invention.

Figure 5:
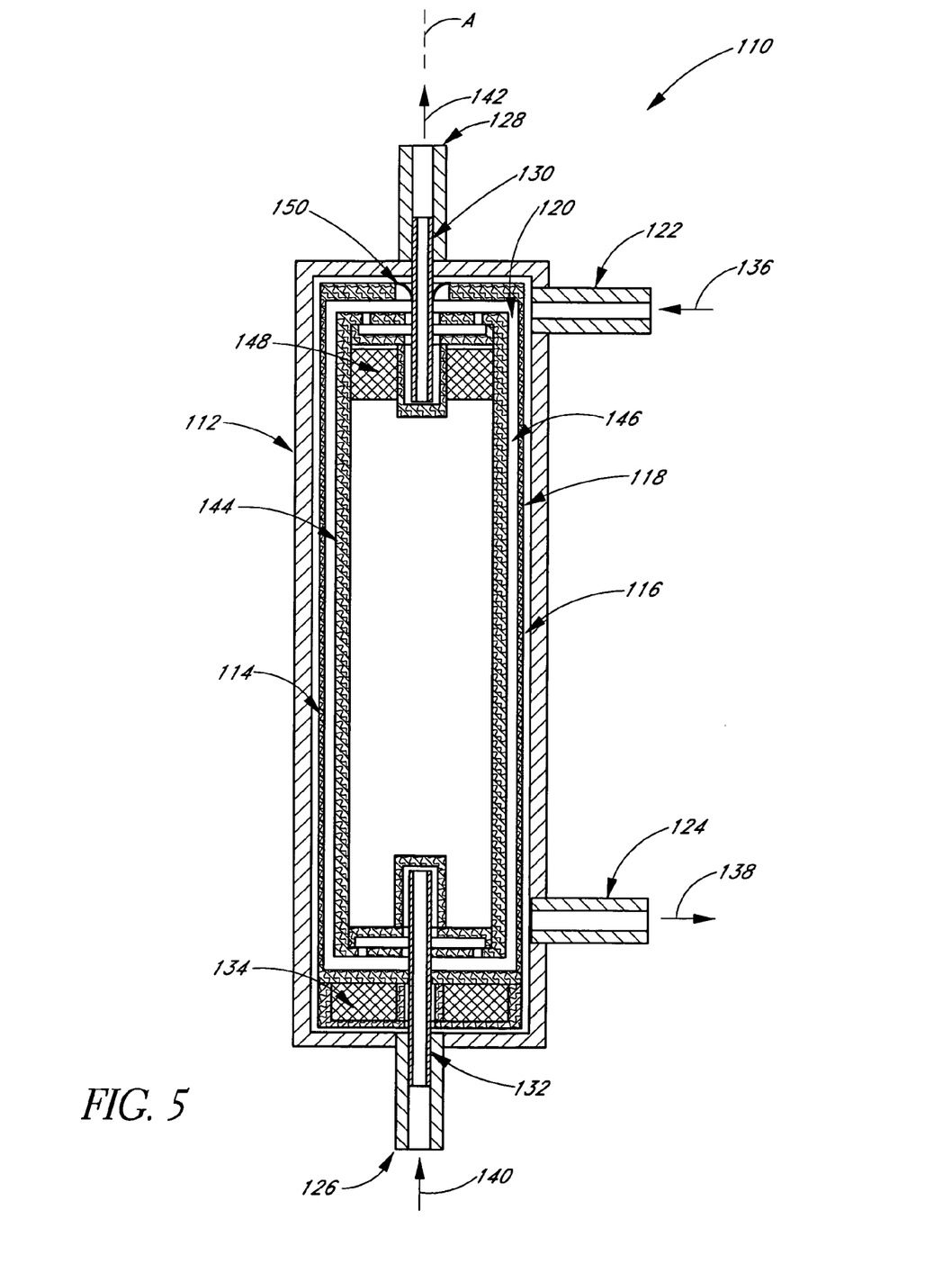
FIG. 5 shows a cross sectional view of one embodiment of a dual rotor vortex-enhanced device of the present invention.

FIG. 5 shows a cross section of another possible embodiment for use with the present invention, in which a dual rotor device creates Taylor vorticity. This illustrated device may preferably be used in a two-stage blood dialysis system, such as that described in detail with reference to FIG. 8. In the illustrated embodiment, the filtration device 110 is used to perform hemodialysis, filtering undesirable waste products from blood into a dialysis fluid, or "dialysate." In other embodiments, the device 110 may be used, more generally, to transfer mass from one fluid to another. In still other embodiments, the device 110 may be used to transfer heat from one fluid to another. As would be well known to those of skill in the art, the invention should not be limited to medical applications.

In one embodiment, the filtration device 110 comprises a cylindrical case 112 housing a cylindrical outer rotor 114. A first gap 116 exists between the case 112 and the outer rotor 114 through which blood flows, and, in a preferred embodiment, the outer rotor 114 is disposed coaxially within the cylindrical case 112. In other embodiments, different geometries and configurations may be chosen for the case and rotor, as discussed above with reference to FIGS. 2-4.

In the illustrated embodiment, the cylindrical, circumferential walls of the outer rotor 114 are at least partially composed of a filtration membrane 118, and partially define an outer rotor interior 120. The outer rotor interior 120 is further defined by the top and bottom walls of the outer rotor 114, which may or may not comprise filtration membrane. As illustrated in FIG. 5, the filtration membrane 118 is a dialysis membrane. This dialysis membrane 118 preferably facilitates the diffusion of molecules smaller than approximately 10,000 Daltons, and the device 110 may thereby function as the first-stage device in the two-stage blood dialysis system illustrated in FIG. 8. In other embodiments, varying degrees of filtration and/or heat transfer may be facilitated by the use of different filtration membranes. For example, in a heat transfer application, the filtration membrane may comprise an impermeable structure, which nevertheless is an effective transferor of heat.

In one embodiment, mounted in the axis A of the cylindrical case 112 are two pivot pins 130, 132, one on either end. These pivot pins 130, 132 define the axis of rotation A for the outer rotor 114, and facilitate the free rotation of this rotor 114. As illustrated, the pivot pins 130, 132 may also be hollow, providing fluid transport passages through the case 112 and outer rotor 114. In other embodiments, other means of facilitating rotation may be provided, including, e.g., ball-bearing assemblies and other means well known to those of skill in the art.

In one embodiment of the invention, the outer rotor 114 can rotate freely within the cylindrical case 112. In order to control this rotation, a spinner magnet 134 may be mounted internally to the outer rotor 114, and an external rotating magnetic field (not shown) may be configured to interact with this spinner magnet 134. By modulating the external magnetic field, the magnet 134 and, in turn, the outer rotor 114 can be made to spin in different directions and at varying speeds. In a preferred embodiment of the invention, the outer rotor 114 can be spun at a speed sufficient to create Taylor vorticity within a fluid in the first gap 116 between the outer rotor 114 and case 112. By creating Taylor vorticity in this first gap 116, filtration performance can be dramatically improved. Other means of spinning the outer rotor 114 in order to create Taylor vorticity may be used in keeping with this invention, as is known to those of skill in the art. For example, in one embodiment, a motor may be attached to at least one of the pivot pins, e.g. upper pivot pin 130, attached to the outer rotor 114.

Inside the outer rotor 114, an inner rotor 144, also supported by the upper and lower pivot pins 130, 132, may be mounted coaxially, with a second gap 146 created between the two rotors 114, 144. Although the inner rotor 144 may partially comprise another filtration membrane, in a preferred embodiment, the inner rotor is relatively impermeable, simply defining the second gap between the two rotors 114, 144. As described in further detail above with respect to the outer rotor and case, the inner rotor 144 may also have differing cross-sectional geometries, and may be mis-aligned to accommodate other fluids and other means of generating Taylor vorticity. In these alternative embodiments, the inner rotor 144 may be supported by structures other than those supporting the outer rotor 114, and may spin about a different axis.

In a preferred embodiment, the inner rotor 144 rotates freely within both the outer rotor 114 and cylindrical case 112. In order to control this rotation, a second spinner magnet 148 may be mounted internally to the inner rotor 144, and a second external rotating magnetic field (not shown) may be configured to interact with this second spinner magnet 148. In the illustrated embodiment, the second spinner magnet 148 for the inner rotor 144 is located at the top of the device 110, and the spinner magnet 134 for the outer rotor 114 is located at the bottom of the device 110. Thus, two separate and independent magnetic fields can control the rotation of the two rotors 114, 144. As described in further detail above, the second spinner magnet 148 mounted to the inner rotor 144 may be controlled similarly to the one mounted to the outer rotor 114. In a preferred embodiment, the inner rotor 144 can be spun at a speed sufficient to create Taylor vorticity within a fluid in the second gap 146 between the inner and outer rotors. In a further preferred embodiment, the inner rotor 144 is spun in a direction opposite the outer rotor 114 to create even more powerful Taylor vortices. By creating Taylor vorticity in this second gap 146, filtration performance can be further improved, as concentration polarization is prevented on the side of the filtration membrane 118 facing the inner rotor 144. Other means of spinning the inner rotor 144 in order to create Taylor vorticity may be used, as is known to those of skill in the art. For example, in one embodiment, a motor may be attached to at least one of the pivot pins, e.g. lower pivot pin 132, attached to the inner rotor 144.

In one embodiment, the rotating magnetic fields that control the two rotors can be produced by a series of magnetic coils that surround the filtration device 110 at its top and bottom. Since pre-connected tubing (not shown) enters and exits the device 110 on axis A in the illustrated embodiment, these electrical coil assemblies can be formed in half arch ("C" sections) that can be closed around the device 110.

The illustrated size of the device 110 is considered adequate for hemodialysis, although in other applications, larger or smaller filtration devices may be utilized to suit the particular fluids being processed.

In a hemodialysis application, the first gap 116 between the outer rotor 114 and inside wall of the case 112 is selected to provide adequate Taylor vorticity in the blood. This first gap 116 depends on the diameter and the RPM of the outer rotor 114, which parameters can be modified by one of skill in the art. With a centrifugal speed in the range of about 1000-5000 RPM and an outer rotor diameter of about 0.1 to 10 inches, the width adequate to generate Taylor vortices may be in the range of about 0.003 to about 0.3 inches. More preferably, a first gap 116 having a width of about 0.03 inches should provide adequate vorticity for an outer rotor 114 of about 1 inch in diameter spun at about 2,400 RPM.

In the illustrated embodiment, the second gap 146 between the inner and outer rotors is selected to provide adequate Taylor vorticity in the dialysate. This second gap 146 depends on the diameters and the RPM difference between the inner and outer rotors. With a centrifugal speed in the range of about 1000-5000 RPM and an inner rotor diameter of about 0.1 to 10 inches, the width adequate to generate Taylor vortices between the inner rotor 144 and outer rotor 114 may be in the range of about 0.003 to about 0.3 inches. Preferably, a second gap 146 having a width of about 0.03 inches should create adequate vorticity for an inner rotor diameter of about 0.8 inches spun at about 3,600 RPM. This preferred set of parameters would give a rotating speed of the inner rotor 144 relative to the outer rotor 114 of about 1,200 RPM. Alternatively, by spinning the inner rotor 144 in the opposite direction of the outer rotor 114, powerful Taylor vorticity can be created in the dialysate.

For the various potential applications, the dimensions and speeds of the inner and outer rotors and casing may be dramatically different. For example, in certain industrial applications, the filtration device 110 may be designed on a much larger-scale in order to accommodate larger flows and liquids of varying viscosity. Optimizing the ranges of gap and rotor sizes, as well as centrifugal speed and rotor direction can be done by one of skill in the art based on the teaching herein.

In the illustrated embodiment, the cylindrical case has four fluid access ports 122, 124, 126, 128. A first inlet port 122 is located at the top of the cylindrical case 112, and a first outlet port 124 is located at the bottom. In a hemodialysis application, this allows blood to flow from top to bottom through the first gap 116 simply using gravitational energy, and pressure from the blood influx. The device 110 is preferably designed such that in the time it takes a certain quantity of blood to travel from the top of the hemodialysis device 110 to the bottom, the desired amount of waste by-product has been extracted. A second inlet port 126 is located at the bottom of the outer rotor 114, and a second outlet port 128 is located at the top of the outer rotor 114. In the hemodialysis application, the dialysis fluid flows through these ports from the bottom of the device 110 to the top through the second gap 146 between the inner and outer rotors. In this preferred embodiment, the fluid paths are designed to take advantage of counter-current mass transfer, meaning that the paths of blood and dialysate are opposite. Fresh dialysate is exposed through the dialysis membrane 118 with mostly dialyzed blood, where the concentration gradient is the lowest. As is well known to those of skill in the art, however, other numbers and configurations of fluid access ports may be used in keeping with the present invention.

Since the first inlet and outlet ports 122, 124 are on the outer diameter of the case 112, there is no need for high pressure on that flow path. This being the case, in the illustrated embodiment, blood will not be forced to the center of rotation of the outer rotor 114, thus fluid seals are not necessary there to prevent blood from entering the inner rotor 144. Fluid seals can be added if higher fluid pressures are employed in hemodialysis or other applications, or if fluids for filtering enter the inner rotor 144 for any reason.

In a preferred embodiment, the second inlet port 126 for dialysate is configured so that the dialysate passes through the lower pivot pin 132 and is then directed into the second gap 146 between the inner and outer rotors, and not downward into the first gap 116 between the outer rotor 114 and case 112. A fluid seal 150 at the top pivot pin 130 is included in the illustrated embodiment to prevent migration of dialysate into the first gap 116 between the outer rotor 114 and case 112. This seal 150 can be any conventional polymer lip seal. As is well known to those of skill in the art, other seals may be implemented. In an alternative embodiment, another fluid seal is included at the bottom pivot pin 132.

In one method of practicing the present invention, blood is exposed to the dialysis membrane 118 with Taylor vorticity resulting in a minimal concentration polarization layer in the first gap 116 between the outer rotor 114 and case 112, maximizing the ability to remove low molecular weight waste products from the patient's blood. In the process of passing through the filtration device 110, dialysate is also exposed to Taylor vorticity, resulting in a minimal concentration polarization layer near the interior of the dialysis membrane 118, maximizing the ability to mix the low molecular weight waste products into the dialysate flow. In a preferred embodiment, the waste dialysate emerging from the device 110 may then be directed through another filtration device to produce recycled, clean dialysate.

Figure 6:
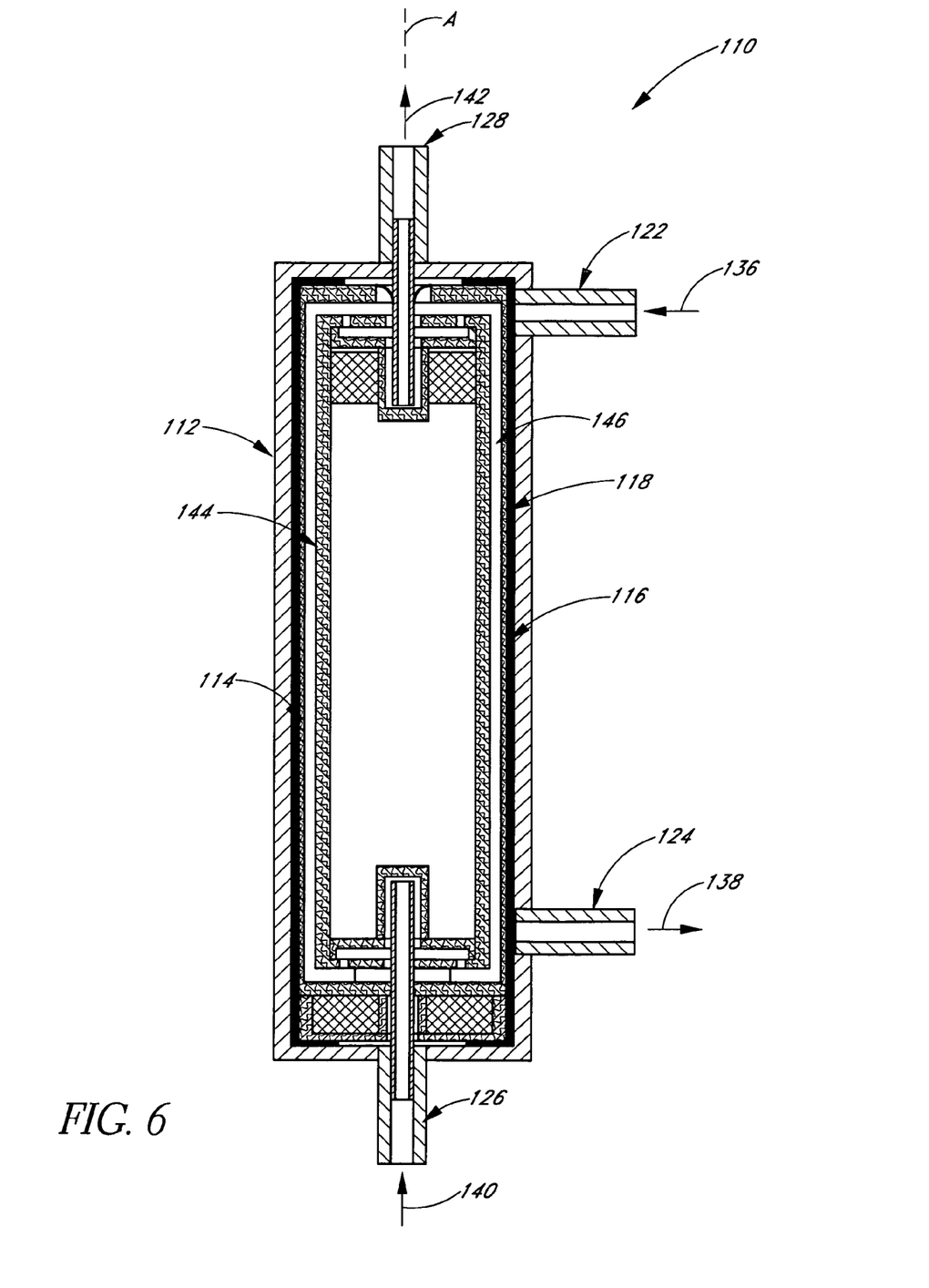
FIG. 6 shows the cross-sectional view of FIG. 5, with the flow-paths of the blood (outer gap) and dialysate (inner gap) highlighted.

In connection with FIG. 6, an exemplary method of performing hemodialysis will be described using the device described in FIG. 5. Within the device 110, the inner and outer rotors are spinning in opposite directions at speeds sufficient to create Taylor vortices in fluids between the outer rotor 114 and case 112, and between the inner rotor 144 and outer rotor 114. Blood is collected from the patient at a particular flow rate 136, and enters the hemodialysis device 110 through the blood inlet port 122, located at the top of the device 110. Dialysis fluid also enters the hemodialysis device 140, but from the bottom, through a second, dialysate inlet port 126. The two fluids are subjected to the forces from the rotors, and Taylor vortices form within them. Thus, concentration polarization is largely alleviated at the dialysis membrane 118 of the outer rotor 114, and a more constant flow of waste products travels through the membrane 118 into the dialysate. The dialysate travels through the hemodialysis device 110, within the second gap 146 between the outer and inner rotors, and exits the top through a dialysate outlet port 128, while the processed blood exits through the blood outlet port 124 at the bottom of the device 110 and is returned to the patient.

In other embodiments, other Taylor vortex-enhanced filtration devices may be used, as further discussed in the co-pending U.S. patent application Ser. No. 10/797,510, which application is herein incorporated by reference in its entirety.

One problem with many of the above described methods of hemodialysis is that the dialysis membrane may be porous to water as well as waste products. Thus, large volumes of plasma water accompany waste products traveling through the dialysis membrane, and the flow of processed blood exiting through the blood outlet port is dramatically reduced from the blood entering the hemodialysis device. This problem is especially acute with respect to the filtration device 10 illustrated in FIG. 1. In one embodiment, a sterile replacement fluid may be added to the processed, dialyzed blood at a junction prior to return to the patient. However, this embodiment risks patient exposure to contaminated replacement fluid, and increases the costs of hemodialysis by the cost of the replacement fluid.

Figure 7A:
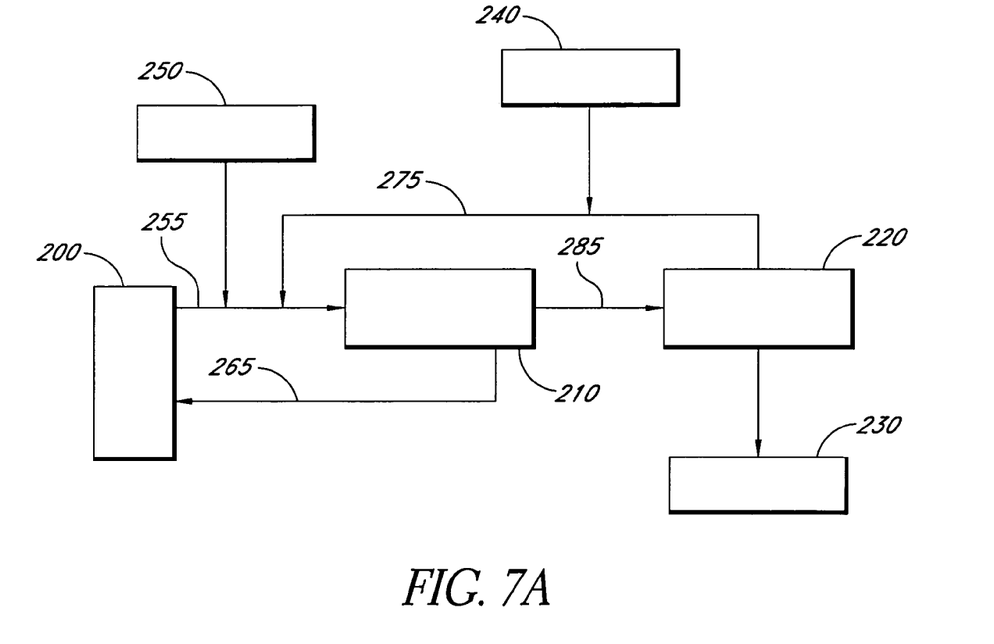
FIG. 7*a* shows a schematic illustration of a filtration dialysis system, wherein replacement fluid is generated from the patient's blood-waste and combined with the blood being drawn from the patient.
Figure 7B:
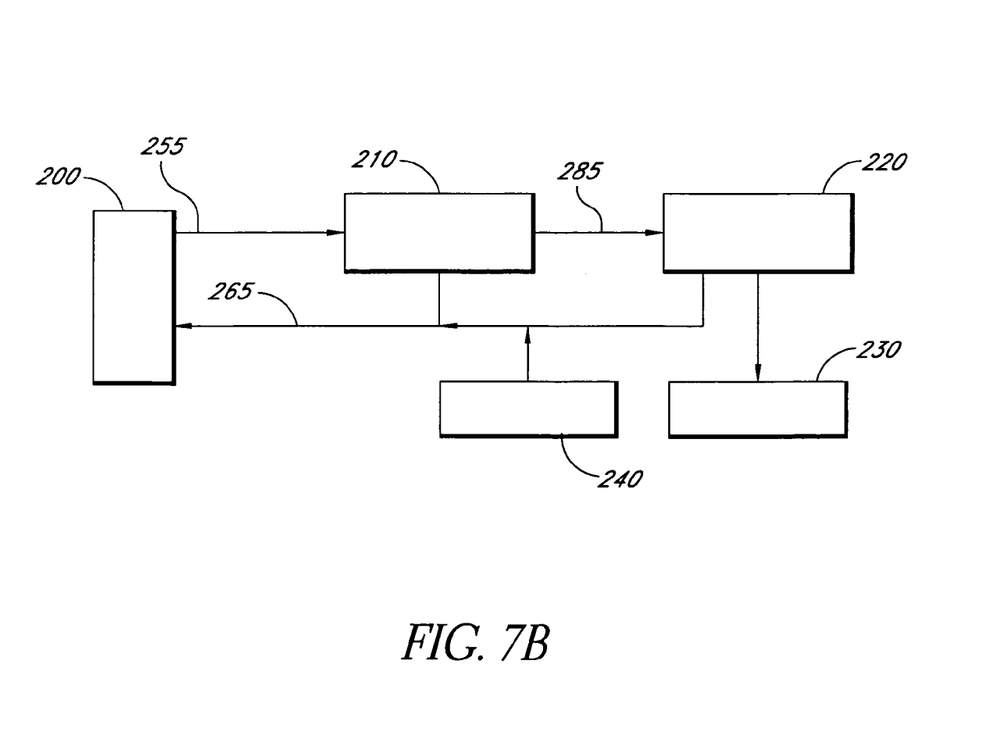
FIG. 7*b* shows a second schematic illustration of a filtration dialysis system, wherein the replacement fluid is generated from the patient's blood-waste and combined with processed blood prior to returning to the patient.

FIGS. 7A and 7B are schematic illustrations of alternate embodiments of two-stage blood dialysis systems according to the present invention, wherein replacement fluid is generated from the blood-waste emerging from a first stage filtration device, reducing the need for artificial replacement fluid. The illustrated embodiments differ in the ordering of steps by which this goal is accomplished but share many operative features. Therefore, the components of these two systems will be discussed together, and the differences will be highlighted, as necessary, in the following discussion. The directions of the flows of various fluids flowing through the systems are illustrated by arrows.

A patient is represented by the box 200 farthest to the left. In a typical implementation, the patient 200 may have a kidney disease that is producing uremic metabolic abnormalities. It is believed that this is due to the fact that intermediate molecular weight molecules (300-6,000 Daltons), removed by healthy kidneys, are producing a morbid toxicity in these patients. In order to alleviate this accumulated toxicity, such a patient 200 typically undergoes periodic dialysis procedures, which remove these intermediate weight molecules. In other embodiments, it may be understood by those of skill in the art that the patient 200 may have another disease in which dangerous or harmful substances are present in the patient's blood. In still other embodiments, the source of the fluid that will be filtered need not be a patient. The process may be used in an industrial setting, for example, in which the fluid is some heterogeneous mixture from which intermediate sized molecules must be extracted.

The device used for the first stage of this two-stage blood dialysis system may be described as a blood filtration device 210. As described above, such a device 210 generally produces filtrates of molecules smaller than a certain size. As is well-known to those of skill in the art, the filtration membrane used in the device 210 can have a wide variety of characteristics and can be chosen to filter any of a number of different sized particles. In one embodiment, the blood filtration device 210 is configured to filter out those molecules having a weight of 10,000 Daltons or less. In this embodiment, the filtrate will preferably include those intermediate weight molecules that are toxic to the patient 200.

The device used for the second stage of this two-stage blood dialysis system may be described as an ultrafiltration device 220, so called because it is permeable to smaller molecules. In a preferred embodiment, the purpose of the ultrafiltration device 220 is to filter out the intermediate weight, toxic molecules from a heterogeneous solution, leaving only water and other small desirable molecules. In the preferred embodiment, the filtration membrane used in the ultrafiltration device 220 is chosen to allow molecules having a weight less than approximately 300 Daltons to pass, thereby separating the potentially toxic waste products from the rest of the solution. In other embodiments, the filtration membrane may only allow molecules having a weight less than approximately 200 Daltons to pass, preventing other, questionably toxic molecules from emerging as filtrate.

The same or different types of filtration devices may be used for the blood filtration device 210 and ultrafiltration device 220. They may comprise, for example, conventional hollow fiber dialysis membrane cartridges, or other filtration devices well known to those of skill in the art. In a preferred embodiment, the devices are Taylor vortex-enhanced filtration devices that function similarly to the filtration device 10 described above with reference to FIG. 1. As described above, these filtration devices may have any combination of a variety of sizes, shapes and speeds for their respective rotors and housings, in order to accommodate the different viscosities and flow rates of the processed fluids.

A waste bag 230 is used to collect the undesirable waste products produced by this two-stage blood dialysis system. In one embodiment, this waste bag 230 should collect many of the same waste products that would normally be collected by a healthy kidney. Of course, the waste bag 230 may represent any of a number of means for collecting and/or disposing of waste and need not be a physical receptacle of any particular shape or size. Often, the waste bags 230 must be collected as hazardous waste for careful disposal according to applicable laws and regulations. Due to the unique features of the present invention, the volume of the waste products generated by the two-stage blood dialysis system may be far less than that generated by a typical single-stage dialysis procedure.

Supplemental replacement fluid sources 240 are also shown in FIGS. 7A and 7B, although they are shown at different locations in the two systems. Although much of the replacement fluid necessary to keep the patient's blood volume constant may be generated from the patient's own blood-waste, there may remain a need for relatively small amounts of artificial replacement fluid during the procedure. Even if the two-stage filtration system functioned perfectly, the volume represented by the intermediate-weight waste molecules should typically be replaced in order to keep the patient's blood volume constant. In one embodiment, it is estimated that approximately three liters of artificial replacement fluid must be added to the patient's blood flow every three hours, as approximately three liters of waste products are removed over the same time frame. This would represent a significant improvement over the 20-30 liters needed during a typical procedure, as described above.

The supplemental, artificial replacement fluid may be generated in a number of ways, but must be sterile, pyrogen-free and generally at body temperature. In one embodiment, artificial replacement fluid may be produced from common tap water as shown in "Successful Production of Sterile Pyrogen-Free Electrolyte Solution by Ultrafiltration," *Kidney International*, 14, 522-25, 1978, a paper by Lee Henderson and Erminia Beans, which is hereby incorporated by reference in its entirety. In other embodiments, such fluid may be produced by other methods well known to those of skill in the art.

In FIG. 7A, an optional component of a two-stage blood dialysis system is shown: an anticoagulant source 250. This anticoagulant source 250 may comprise a source for heparin, for example, that is mixed with blood to prevent the blood from coagulating extracorporeally. In other embodiments, other means for facilitating filtration, and for preventing clumping or other undesirable fluid characteristics may be employed. For example, water may be added to other heterogeneous solutions to facilitate the production of vortices in the filtration devices 210, 220.

Using the two-stage blood dialysis system illustrated in FIG. 7A, a method of performing blood dialysis according to the present invention may now be discussed in further detail. The first step in the procedure is drawing blood from the patient, illustrated by the arrow 255 extending from the patient 200 to the blood dialysis filtration device 210. Conventionally, blood is drawn from the patient 200 via an IV tube connected to a patient's artery in the patient's arm. Of course, other means of drawing blood from a patient are well-known to those of skill in the art. As discussed above, a typical rate of blood flow from the patient is 300-450 mL/min. In order to keep the patient's blood volume relatively constant, therefore, the fluid returning to the patient, arrow 265, must flow at a similar rate. Conventionally, the fluid returning to the patient 200 is returned through an IV tube connected to the patient's vein.

In an optional second step, the blood flowing from the patient 200 is mixed with an anticoagulant from an anticoagulant source 250. In this way, performance of the blood dialysis system may be improved.

The blood that is flowing from the patient 200 is then passed through the blood dialysis filtration device 210. The filtration device 210 may filter the blood in a number of ways well known to those of skill in the art. In a preferred embodiment, the filtration device 210 works similarly to the device 10 described in detail above. In this implementation, the blood flows into the gap 16 between the case 12 and the rotor 14 through the inlet port 22. The filtration membrane 18 is designed to allow molecules with a molecular weight less than approximately 10,000 Daltons to pass into the rotor interior 20. The blood flowing from the patient 200 has a number of constituents, including: water, electrolytes, small nutrient molecules, waste products, high molecular weight molecules (e.g. proteins, etc.) and blood cells and other cells of various types. The first four of the above-listed constituents comprise blood-waste and can pass through the filtration membrane 18 into the rotor interior 20. Thus the rotor interior fills with water, electrolytes and small nutrient molecules, and waste products.

Meanwhile, the rotor 14 spins rapidly enough to create Taylor vortices in the blood flowing through the gap 16 between the rotor 14 and housing 12. These Taylor vortices mix the blood in this gap 16 and thereby alleviate the problem of concentration polarization on the outside portion of the filtration membrane 18.

The filtration device 210 has two outlet ports, 24 and 26. The first outlet port 24 communicates with the gap 16 between the rotor 14 and housing 12. If the blood-waste were not recycled, the blood constituents that were too large to pass through the filtration membrane 18 would pass out of the blood filtration device 210 through the outlet port 24. In a typical implementation, the flow rate from this outlet port 24 would be roughly half the flow rate going into the inlet port 22. Thus, roughly half of the patient's blood comprises water, small desirable molecules, and waste products, and the other half comprises larger molecules and cells which pass out through outlet port 24. These larger components would be represented by the arrow 265 leading back to the patient 200.

However, since the water and small desirable molecules are recycled back into the two stage system as replacement fluid, as shown by the arrow 275, the blood filtration device 210 is unable to filter the incoming fluid completely, and the arrow 265 representing the processed blood and replacement fluid returning to the patient comprises a volume at least roughly equivalent to the blood flow 255 coming from the patient 200. The return flow 265 thereby comprises both larger components and replacement fluid without undesirable waste products. Further details of this process are discussed below.

The second outlet port 26, which is in communication with the rotor interior 20, conducts a flow 285, roughly half that of the blood flow 255 from the patient, comprising water, small desirable molecules, and waste products. This flow of blood-waste 285 enters the ultrafiltration device 220.

As described above, the ultrafiltration device 220 may function similarly to the filtration device 10. The filtration membrane 18 of the ultrafiltration device 220 is configured such that water and small desirable molecules enter the rotor interior 20 of the ultrafiltration device 220. The intermediate weight waste products are filtered out and pass from the ultrafiltration device 220 to the waste bags 230, as represented by the arrow 285. The filtrate, meanwhile, now comprises a clean, warm, bio-compatible replacement fluid that can be used to increase the volume of blood that is returning to the patient.

In the embodiment shown in FIG. 7A, this patient-generated replacement fluid flow 275 is recycled to the beginning of the two-stage filtration system, where a T-junction mixes the replacement fluid flow 275 and the flow from the patient 255. The T-junction may be any of a number of devices that mix two fluid inputs and have one fluid output, as is well known to those of skill in the art. In one embodiment, the T-junction simply comprises T-shaped sections of tubing. The amount of fluid entering the blood dialysis device 210 is thereby increased, and the flow 265 back to the patient 200 is also increased. Since there may be a reduction in flow due to the loss of waste products, a small amount of artificial, supplemental replacement fluid 240 may also be introduced. According to a preferred embodiment of the present invention, the flow 265 returning to the patient 200 approximates the flow 255 exiting the patient 200, and the patient's blood volume is kept relatively constant.

In a preferred embodiment, the replacement fluid can be supplemented with a variety of additives. Typical additives include biologically compatible buffers, such as bicarbonate, lactate, citrate, and acetate. Other components, such as chloride, sodium, calcium, magnesium, potassium, phosphate, dextrose, and glucose, or any other molecule required by the particular patient, may also be added to the replacement fluid.

The implementation illustrated in FIG. 7B is very similar to the one described above with respect to FIG. 7A. The sole difference lies in the location of the T-junction, at which the patient-generated replacement fluid flow 275 reenters the system. In FIG. 7B, this flow 275 is combined with the flow of processed blood returning to the patient 200. Thus, the return flow 265 is increased to approximate the extraction flow 255, immediately before reintroduction to the patient. In a preferred embodiment, flow meters may be placed at various points in the two-stage systems of FIGS. 7A and 7B in order to monitor fluid flows, and to provide feedback regarding the need for supplemental artificial fluid, for example. As is well-known to those of skill in the art, a variety of flow meters may be used, provided that they are sterile and configured for use in a hospital environment.

In both of these Figures, the blood dialysis device 210 can utilize hemofiltration or hemodiafiltration, including continuous veno-venous hemofiltration and continuous arteriovenous hemofiltration.

Although FIGS. 7A and 7B describe continuous processes, it is to be understood that batch processes are embraced. Batch processes include processing portions of blood removed from patients. The blood can then be processed to selectively remove components from the generated replacement fluid. The processed blood can be combined with the replacement fluid and returned to the patient.

In another embodiment, dialysate can be recycled in a two-stage blood dialysis system. Typically, dialysate is disposed of after a single run through a dialysis device, such as filtration device 110, once it has been contaminated by waste products. As a result, prior art dialysis devices suffer from many of the same inefficiencies discussed above with respect to filtration devices; large volumes of replacement dialysate are necessary, and large volumes of waste are generated. Instead, according to one embodiment of the present invention, the dialysate containing the intermediate weight waste products can be sent through a second filtration device, such as one of filtration devices 10 or 110, in order to separate the waste products from the dialysate. The recycled dialysate emerging as filtrate from this second filtration device can then be used in further dialysis procedures.

Figure 8:
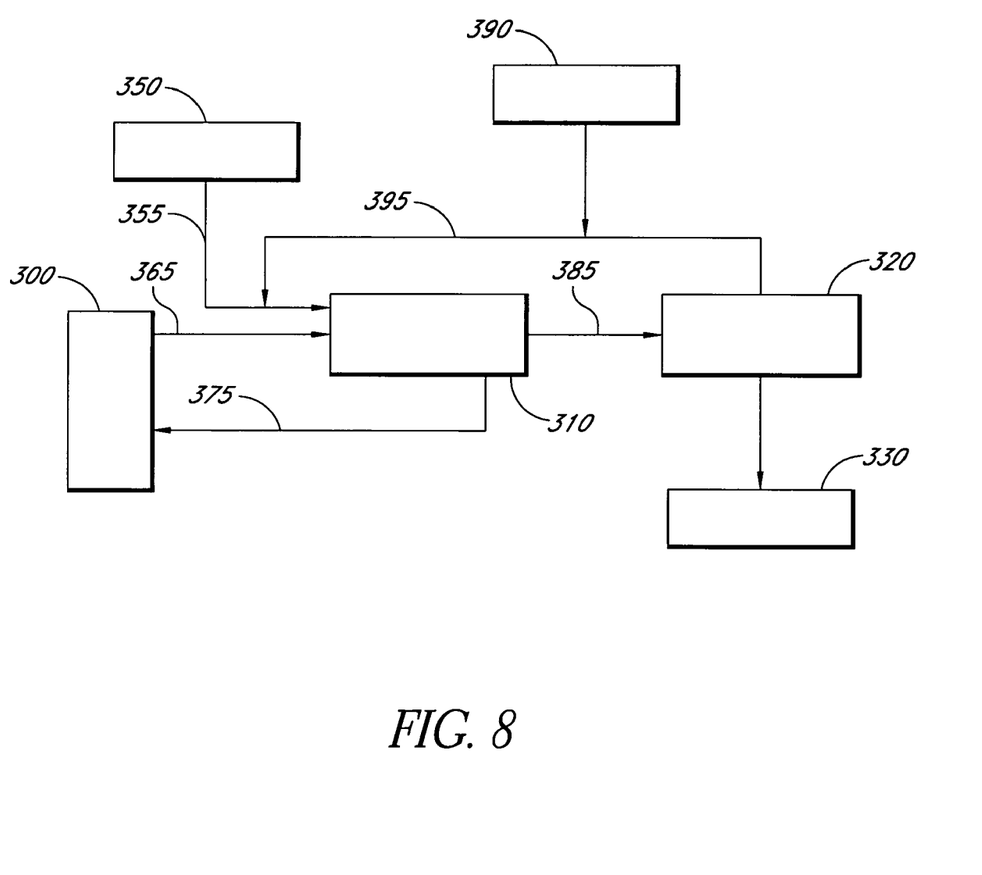
FIG. 8 shows a schematic illustration of a filtration dialysis system, wherein recycled dialysate is obtained from waste dialysate flowing from a dialysis device.

FIG. 8 is a schematic illustration of such a two-stage blood dialysis system, wherein clean, recycled dialysate is generated from waste dialysate, reducing the need for large volumes of replacement dialysis fluid. As above, the directions of the flows of various fluids flowing through the system are illustrated by arrows.

A patient is represented by the box 300 farthest to the left. In a typical implementation, the patient 300 has characteristics similar to those discussed above with respect to patient 200. Alternatively, the two-stage system may be used in an industrial setting, in which the filtered fluid is some heterogeneous mixture from which intermediate sized molecules must be extracted.

The device comprising the first stage of this two-stage blood dialysis system is hemodialysis device 310. As is well-known to those of skill in the art, the filtration membrane used in the device 310 can have a wide variety of characteristics and can be chosen to filter any of a number of differently sized particles. In one embodiment, the hemodialysis device 310 is configured to allow only those molecules having a weight of 10,000 Daltons or less to diffuse across the membrane.

In general, a hemodialysis device, as discussed above, has two liquids running therethrough, one on either side of a filtration membrane. Since aqueous solutions are present on both sides of the membrane, the volumes of the liquids stay roughly the same, but the molecules therein tend to equilibrate across the membrane, as long as they can diffuse through. Thus, dialysate, having a relatively high concentration of electrolytes, salts, and other small desirable molecules, may be sent along one side of the filtration membrane, and the patient's blood, having a high concentration of waste by-products, may be sent along the other side of the filtration membrane. The two solutions will move towards equilibrium with respect to the molecules that can diffuse across the membrane, and the result will typically be a solution of dialysate and waste products, and processed blood with additional small desirable molecules.

The device used for the second stage of this two-stage blood dialysis system may be described as an ultrafiltration device 320, so called because it is permeable to smaller molecules. In a preferred embodiment, the purpose of the ultrafiltration device 320 is to filter out the intermediate weight, toxic molecules from a heterogeneous solution, leaving only the dialysate and other small desirable molecules. In the preferred embodiment, the filtration membrane used in the ultrafiltration device 320 is chosen to allow molecules having a weight less than approximately 300 Daltons to pass, thereby separating the potentially toxic molecules from the rest of the solution. In other embodiments, the filtration membrane may only allow molecules having a weight less than approximately 200 Daltons to pass, preventing other, possibly toxic molecules from emerging as filtrate.

The same or different types of filtration devices may be used for the hemodialysis device 310 and ultrafiltration device 320. As is well-known to those of skill in the art, a number of possible hemodialysis devices and filtration devices may be used. In a preferred embodiment, the hemodialysis device 310 is a Taylor vortex-enhanced filtration device that functions similarly to the filtration device 110 described above with reference to FIGS. 5 and 6. The ultrafiltration device 320 is preferably a Taylor vortex-enhanced filtration device similar to the filtration device 10 described above. As described above, these filtration devices may have any combination of a variety of sizes, shapes and speeds for their respective rotors and housings, in order to accommodate the different viscosities and flow rates of the processed fluids.

A waste bag 330 is used to collect the undesirable waste products produced by this two-stage blood dialysis system. In one embodiment, this waste bag 330 should collect many of the same waste products that would normally be collected by a healthy kidney. Of course, the waste bag 330 may represent any of a number of means for collecting and/or disposing of waste and need not be a physical receptacle of any particular shape or size. Often, the waste bag 330 must be collected as hazardous waste for careful disposal according to applicable laws and regulations. Due to the unique features of the present invention, the volume of the waste products generated by the two-stage blood dialysis system may be far less than that generated by a typical single-stage hemodialysis procedure.

Dialysate source 350 is shown with dialysate flow 355 entering the hemodialysis device 310. In one embodiment, the dialysate flow 355 entering the hemodialysis device 310 is roughly equivalent to the blood flow 365 from the patient. Thus, the processed blood flow 375 back to the patient 300 is not substantially reduced in comparison to the flow from the patient. As discussed above, the dialysate flowing through the device 310 will travel along the other side of a filtration membrane from the blood flowing through the device 310. In order to encourage the diffusion of waste products and prevent blood contamination, the dialysate should be sterile, pyrogen-free and generally at body temperature.

In a preferred embodiment, the dialysate is supplemented with a variety of additives. Typical additives include biologically desirable components, such as chloride, sodium, calcium, magnesium, potassium, phosphate, dextrose, and glucose, or any other molecule required by the particular patient. These smaller molecules can diffuse across the filtration membrane into the processed blood returning to the patient.

Using the two-stage blood dialysis system illustrated in FIG. 8, a method of performing blood dialysis according to the present invention may now be discussed in further detail. The first step in the procedure is drawing blood from the patient, illustrated by the arrow 365 extending from the patient 300 to the hemodialysis device 310. Conventionally, blood is drawn from the patient 300 via an IV tube connected to a patient's artery in the patient's arm. Of course, other means of drawing blood from a patient are well-known to those of skill in the art. As discussed above, a typical rate of blood flow from the patient is 300-450 mL/min. In order to keep the patient's blood volume relatively constant, therefore, the fluid returning to the patient, arrow 375, should flow at a similar rate. Conventionally, the fluid returning to the patient 300 is returned through an IV tube connected to the patient's vein.

The blood that is flowing from the patient 300 is then passed through the hemodialysis device 310. The hemodialysis device 310 may dialyze the blood in a number of ways well known to those of skill in the art. In a preferred embodiment, the hemodialysis device 310 works similarly to the device 110 described in detail above. In this implementation, the blood flows into the first gap 116 through the inlet port 122. Dialysate flows into the second gap 146 through the inlet port 126.

The filtration membrane 118, separating the second gap 146 from the first gap 116, is designed to allow molecules with a molecular weight less than approximately 10,000 Daltons to pass in either direction. The blood flowing from the patient 300 has a number of constituents, including: water, electrolytes, small nutrient molecules, waste products, high molecular weight molecules (e.g. proteins, etc.) and blood cells and other cells of various types. The dialysis fluid flowing from the dialysate source 350 includes water and other small desirable molecules that might supplement the patient's processed blood. Thus, as the dialysate and blood flow in opposite directions through the hemodialysis device 310, the blood accumulates the small desirable molecules diffusing from the dialysate, and the dialysate accumulates the waste products diffusing from the blood.

Meanwhile, the rotors 144, 114 spin rapidly in order to create Taylor vortices in both the blood flowing through the first gap 116, and in the dialysate flowing through the second gap 146. These Taylor vortices mix the fluids in both gaps and thereby alleviate the problems of concentration polarization on the outside and inside of the filtration membrane 118.

The filtration device 310 has two outlet ports, 124 and 128. The first outlet port 124 communicates with the first gap 116. Because very little water diffuses across the filtration membrane 118 (since the dialysate and blood have relatively equivalent flows), in a typical implementation, the flow rate from this outlet port 124 is roughly equal to the flow rate into the inlet port 122. If there are small discrepancies, they can be rectified using supplemental replacement fluid or by removing a small quantity of the processed blood before return to the patient.

The second outlet port 128, which is in communication with the second gap 146, conducts the flow of waste dialysate 385. This waste dialysate 385 enters the ultrafiltration device 320.

As described above, the ultrafiltration device 320 may function similarly to the filtration device 10. The filtration membrane 18 of the ultrafiltration device 320 is configured such that the dialysate substrate and small desirable molecules enter the rotor interior 20 of the ultrafiltration device 320. The intermediate weight waste products are filtered out and pass from the ultrafiltration device 320 to the waste bags 330. The filtrate, meanwhile, now comprises a clean, warm, bio-compatible dialysate that can be used once again to diffuse waste products from the patient's blood.

Since the concentration of small desirable molecules in the dialysate has been depleted by diffusion into the patient's processed blood, these molecules may be supplemented from a small desirable molecule source 390. In a preferred embodiment, the system may detect the flow of dialysate and add appropriate amounts of concentrated liquid to the recycled dialysate through a T-junction.

In the embodiment shown in FIG. 8, the recycled dialysate 395 is introduced at the beginning of the two-stage filtration system, where a T-junction combines the recycled dialysate 395 and the new dialysate flow 355. Ideally, very little unused dialysate will be needed once the system has gone through a complete cycle.

In variations of the embodiments illustrated in FIGS. 1-8, this invention can be applied to a vast number of other applications. In a general sense, embodiments of this invention can be useful in any application where filters lose performance due to clogging or concentration polarization, and where replacement fluid is desirable. These applications include: removal of salt from water, processing sea water for human consumption, processing sea water for agricultural uses, reprocessing waste water for agricultural uses, reprocessing waste water for human consumption, concentrating sugar or other desired components from sap from plants, such as sugar cane sap or maple sap, concentrating latex from the sap of rubber plants, removing impurities from water for industrial applications, such as needed in the pharmaceutical or electronic industries, recycling cooking oil, recycling motor oil or lubricating oils, and producing sterile water for intravenous injection.

Further, where molecular exclusion or sieving membranes are employed, the device can be used for large scale cell and biotechnology separation applications, such as purifying cell supernatants and/or lysates from cellular material in a bioprocessor or fermentor.

The various materials, methods and techniques described above provide a number of ways to carry out the invention. Of course, it is to be understood that not necessarily all objectives or advantages described may be achieved in accordance with any particular embodiment described herein. Thus, for example, those skilled in the art will recognize that the components of the system may be made and the methods may be performed in a manner that achieves or optimizes one advantage or group of advantages as taught herein without necessarily achieving other objectives or advantages as may be taught or suggested herein.

Although the present invention has been described in terms of certain preferred embodiments, other embodiments of the invention including variations in dimensions, configuration and materials will be apparent to those of skill in the art in view of the disclosure herein. In addition, all features discussed in connection with any one embodiment herein can be readily adapted for use in other embodiments herein. The use of different terms or reference numerals for similar features in different embodiments does not imply differences other than those which may be expressly set forth. Accordingly, the present invention is intended to be described solely by reference to the appended claims, and not limited to the preferred embodiments disclosed herein.

What is claimed is:

1. A system for two-stage blood filtration of a patient, comprising:
   a first filtration device, comprising a blood inlet port connected to a blood supply conduit, a blood waste outlet port connected to a blood waste flow conduit, and a filtered blood outlet port connected to a filtered blood flow conduit; and
   a second filtration device, comprising a blood waste inlet port connected to the blood waste flow conduit, a replacement fluid outlet port connected to a replacement fluid flow conduit, and a waste product outlet port;
   wherein at least one of the first and second filtration devices comprises a Taylor vortex-enhanced filtration device, a downstream end of the replacement fluid flow conduit is connected to either the blood supply conduit or the filtered blood flow conduit, and neither of the first and second filtration devices comprises a dialysis device.

2. The system of claim 1, further comprising a T-junction connecting the replacement fluid flow conduit to the filtered blood flow conduit to create a return blood flow.

3. The system of claim 2, further comprising a supplemental fluid source connected to the filtered blood flow conduit.

4. The system of claim 3, wherein the supplemental replacement fluid is supplemented with at least one additive.

5. The system of claim 2, wherein the return blood flow is substantially equal to blood flow from the patient.

6. The system of claim 1, further comprising a T-junction connecting the replacement fluid flow conduit to the blood supply conduit to increase blood flow entering the first filtration device.

7. The system of claim 6, wherein the blood flow to the first filtration device is further increased by the introduction of a supplemental replacement fluid.

8. The system of claim 7, wherein the supplemental replacement fluid is supplemented with at least one additive.

9. The system of claim 1, further comprising an anticoagulant source for mixing an anticoagulant with the blood from the patient.

10. The system of claim 1, wherein said Taylor vortex-enhanced filtration device comprises:
    a housing having a housing wall;
    a first rotor having a first wall comprising a filtration membrane and defining a first interior, wherein said first rotor is disposed within said housing and is adapted to rotate therein, such that a first gap exists between the filtration membrane and the housing wall; and
    a first rotational drive means for rotating the first rotor within said housing at a speed sufficient to create Taylor vorticity in the first gap.

11. A system for two-stage blood filtration of a patient, comprising:
    a first filtration device for receiving the blood from the patient and producing a first filtrate and processed blood, wherein the first filtration device comprises:
       a cylindrical housing having a housing wall;
       a first cylindrical rotor having a first wall comprising a dialysis membrane, wherein said first cylindrical rotor is disposed coaxially within said housing and adapted to rotate therein, such that a first coaxial gap exists between the dialysis membrane and the housing wall;
       a second cylindrical rotor having a second wall, wherein said second cylindrical rotor is disposed coaxially within said first cylindrical rotor and adapted to rotate therein, such that a second coaxial gap exists between the first and second walls;
       a first inlet port in the housing wall for conducting the blood from the patient into the first coaxial gap and a first outlet port in the housing wall for conducting processed blood out of the first coaxial gap;
       a second outlet port in said housing for conducting the first filtrate out of the second coaxial gap;
       a first rotational drive means for rotating the first cylindrical rotor within said housing; and
       a second rotational drive means for rotating the second cylindrical rotor within said housing; and
    a second filtration device for receiving the first filtrate and producing replacement fluid and waste product;
    wherein at least one of the first and second filtration devices comprises a Taylor vortex-enhanced filtration device.

* * * * *